United States Patent [19]

Neese et al.

[11] Patent Number: 5,046,965

[45] Date of Patent: Sep. 10, 1991

[54] DISPOSABLE ELECTRICAL CONNECTOR FOR FETAL SCALP ELECTRODE

[75] Inventors: Jon N. Neese; William D. Wallace, both of Salt Lake City; Christopher A. Cutler, Centerville, all of Utah

[73] Assignee: Utah Medical Products, Inc., Utah

[21] Appl. No.: 518,809

[22] Filed: May 4, 1990

[51] Int. Cl.$^5$ ............................................. H01R 13/62
[52] U.S. Cl. ............................... 439/372; 439/854; 439/722; 439/729; 439/838; 439/909; 128/642
[58] Field of Search ............... 439/854, 855, 372, 722, 439/725, 410, 342, 338, 838, 859, 909, 346, 729, 889, 711, 713, 691, 697, 596, 597, 696; 128/642, 784

[56] References Cited

U.S. PATENT DOCUMENTS

| | | | |
|---|---|---|---|
| 3,895,635 | 7/1975 | Justus et al. | 439/909 X |
| 4,061,408 | 12/1977 | Bast et al. | 439/729 X |
| 4,094,571 | 6/1978 | Benjamin | 439/859 X |
| 4,253,721 | 3/1981 | Kaufman | 439/372 |
| 4,268,101 | 5/1981 | Stone | 439/729 X |
| 4,384,757 | 5/1983 | Andrews, Jr. et al. | 439/736 |
| 4,671,591 | 6/1987 | Archer | 439/859 X |
| 4,894,023 | 1/1990 | Hall | 439/909 X |
| 4,911,657 | 3/1990 | Berlin | 439/909 X |

FOREIGN PATENT DOCUMENTS 1339029 11/1973 United Kingdom .............. 439/697

Primary Examiner—Larry I. Schwartz
Assistant Examiner—Julie R. Daulton
Attorney, Agent, or Firm—Workman, Nydegger & Jensen

[57] ABSTRACT

An electrical connector of extreme simplicity for coupling leads of a fetal scalp electrode to a cable of an electrical signal monitor. The connector includes a plurality of electrically isolated wiring frame components derived from a single wiring frame and thereafter insert molded into a connector body. The wiring frame components include a pair of signal pathways passing through the connector body to couple each lead of the fetal electrode to a corresponding conductor in the cable and a reference pathway through the connector body for effecting an electrical reference coupling with the body of the patient and communicating a reference voltage through the cable to the monitor. Integrally formed on the connector body is a pivotable lead retention wing and thereon a lead retention stub. By pivoting the retention wing into a position adjacent to the connector body, the retention stub along with a lead of the fetal scalp electrode is received and clamped into a lead retention recess. Other integrally formed features of the connector body facilitate coupling and any decoupling of the retention stub from the retention recess.

33 Claims, 8 Drawing Sheets

DISPOSABLE ELECTRICAL CONNECTOR FOR FETAL SCALP ELECTRODE

BACKGROUND

1. Field of the Invention

This invention relates to electrical connectors for coupling leads from a patient to a monitor for displaying signals appearing on the leads reflecting a condition of the patient. More particularly, the present invention relates to a disposable electrical connector for use with a pregnant patient in labor to couple the leads of a fetal scalp electrode to a remote monitor of the status of the fetal heart beat.

2. Background Art

During medical procedures it is frequently useful to monitor a condition of a patient through a display of electrical signals generated in the body of the patient which are reflective of the condition. To facilitate movement by and around the patient, it is generally desirable that electrical equipment associated with the monitor and the electrical equipment connected to the patient be selectively separable. Nevertheless, when actually utilized, these two components of the monitoring system must be readily and reliably interconnectable.

This is particularly true, for example, in fetal monitoring, which is now commonplace. Electrical signals generated in the fetus are a reliable indicator of the fetal heart beat, which in turn is useful to medical practitioners in detecting fetal distress and in gauging fetal health.

Although useful in other circumstances, the technique of fetal monitoring has and continues to be employed primarily during the time that a pregnant patient is in labor. Typically, one or more electrodes is attached to the scalp of the fetus and then connected by way of leads passing through the birth canal to an electrical monitoring device. Commonly the electrodes take the form of pointed wires bent into a helical shape at the tip of a probe that is inserted through the birth canal into contact with the fetal scalp. Rotation of the probe causes the leads to catch and become embedded in the tissue of the fetal scalp.

In the past it has almost uniformly been the case that a reference electrode is attached directly to the body of the pregnant patient in order to establish a base or reference voltage for use in calibrating and stabilizing the monitor display. This reference electrode has taken a number of forms. Initially a metal plate was wired directly to the monitor and secured using tape in direct contact with the skin of the patient. A conductive gel was used between the plate and the skin of the patient to enhance the electrical contact.

Alternatively, the reference voltage plate was incorporated into an electrical connector which also served to selectively couple the leads from the fetal scalp electrode with a cable connected to the electronic monitor. It was necessary that this type of electrical connector effect secure mechanical and electrical interconnections between the leads from the fetal monitor and corresponding signal conductors in the cable attached to the monitor. In addition, by placing the reference voltage plate of the connector in appropriate contact with the skin of the pregnant patient, the connector developed a reference voltage which in turn was couplable to a reference connector in the cable.

Such electrical connectors were routinely held in place against the abdomen or the thigh of the patient by a belt or strap. Effective electrical contact between the reference voltage plate and the skin of the patient continued to be facilitated through use of a conductive gel. When thusly mounted to the body of a patient, however, the electrical connector exhibited a capacity to migrate away from the site at which the conductive gel had been applied. In addition, the belt or strap by which the connector was held in place came to be perceived as an uncomfortable encumbrance upon the freedom of the patient to move during labor.

Accordingly, an alternative manner of effecting the required reference voltage contact and of holding the connector in place was developed. This involved a disposable adhesive patch which was applied to the skin of the patient. The side of the adhesive pad in contact with the patient was provided with a recess or a pad containing electrically conductive gel. This reservoir of gel was electrically coupled to a male metallic snap fitting on the opposite of the patch. Once applied to the skin of the patient, the adhesive patch provided a site for obtaining the desired reference voltage which would not migrate. The electrical connector was correspondingly provided on the side to be placed in contact with the patient with a female snap fitting recess.

In this way, the electrical connector was mechanically attached to the adhesive pad, preventing its migration. Through electrical conductors located in the cooperating snap fittings, the electrical connector could also reliably couple a reference voltage to the same cable as was used to transmit signals from the fetal electrode to the electronic monitor.

Recent experience and advancement of electronic monitors has lead many practitioners to forego what was formerly a mandatory reliance on the reference voltage. Thus, while some medical personnel continue to use a conductive gel and a reference voltage plate or an adhesive pad and snap, others are content either to use the reference plate without a gel or to forego any reference voltage whatsoever.

While the electrical connectors described above exhibit advances in terms of convenience and reliability over the earliest forms of connectors and reference plates employed in this setting, they are afflicted by a number of disadvantages.

Firstly, such electrical connectors continue to exhibit undesireable mechanical complexity by utilizing a large number of distinct components. For example, most employ one or another form of spring biased clips with which to effect electrical contact with the leads of the fetal scalp electrode. A spring biased approach to this function necessitates at least two components which slide in relation to each other and one or another form of a spring for biasing these into a position which clasps each lead from the fetal electrode. These components are not only distinct from the connector body, requiring mechanical attachment thereto, but must in addition be coupled to electrical wiring therewithin.

Such structural realities are in turn reflected in complex manufacturing procedures and high costs of production. Expense has necessitated that the electrical connectors be reusable, imposing on hospitals the cost of purchasing and maintaining an inventory. Expense is not, however, the only difficulty encountered in known electrical connectors for use in this environment.

Due to the complexity of their construction many electrical connectors are heavy and bulky. This results in their inhibiting patient freedom and in their being difficult to secure at a fixed location. It has been found that spring loaded clips, despite their mechanical complexity, are difficult to couple and uncouple with the appropriate fetal electrode leads. Where miniaturization efforts are undertaken in order to reduce bulkiness and to gain some cost advantage, complex clipping systems become even more difficult to operate.

Thus, the goal of small size runs in some respects counter to that of convenient operation. One factor is traded off for the other, without significantly improving the overall device.

Practitioners are currently divided over the manner in which it is preferred to establish an electrical reference voltage. Electrical connectors adapted for one mode of use are also capable of functioning in the other. Thus, medical personnel must adopt both an electrical connector and a means for obtaining a reference voltage which are in harmony. This limits flexibility. Those practitioners who feel free not to rely on a reference voltage do not appreciate the extra cost occasioned in such electrical connectors by the provision of reference voltage plates or other structures for that purpose.

Thus, in relation to electrical connectors for use in systems employing fetal scalp electrodes, the goals of miniaturization, disposability, versatility, and ease of operation are to various extents in conflict one with another. As a result, an optimum combination has yet to be developed.

BRIEF SUMMARY AND OBJECTS OF THE INVENTION

Accordingly, one object of the present invention is an improved electrical connector for coupling a fetal scalp electrode, and optionally a reference voltage contact, to an electronic display monitor.

Another object of the present invention is an electrical connector as described above which exhibits extreme simplicity in its number of parts and in its manner of manufacturing.

Correspondingly, it is yet another objective of the invention to produce an electrical connector of reduced size and minimal cost so as to be disposable.

In light of these objections, it is a further objective of the present invention to produce an electrical connector of the type described which does not encumber the freedom of the patient with which it is used, but which is reliably securable to the leads of the fetal scalp electrode.

While attaining the above described objects, it is a further object of the present invention that the electrical connector be easy to couple and uncouple from the leads of a fetal scalp electrode.

Another object of the present invention is an electrical connector as described above which does not commit its medical practitioner user to any specific one of the several modes of obtaining a reference voltage.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein a connector is provided for use during labor and delivery to couple signals from the leads of a fetal scalp electrode to a cable connected to an electrical signal monitor. The connector comprises a connector body, a lead retention means that is integrally formed with a connector body for securing the leads of the fetal scalp electrode to the connector body, and conductive means for electrically coupling the leads of the fetal scalp electrode through the connector body to the cable. One lead retention means consistent with the teachings of the present invention comprises a pair of mutually cooperating first and second lead retention structures. These are integrally formed with the connector body at distinct locations on the exterior thereof and are resiliently engageable with each other with a lead of the fetal scalp electrode clasped therebetween.

In a preferred embodiment, the first of the cooperating structures is located on a lead retention wing which itself is integrally formed with and pivotable from the connector body. The second of the cooperating structures is located on the exterior of the connector body at a position opposing the first of the cooperating structures when the lead retention wing is pivoted against the connector body. The first lead retention structure in one form of the invention comprises a lead retention stub, while the second lead retention structure takes the form of a lead retention recess configured to snappingly receive and to resiliently grip the lead retention stub.

In another aspect of the present invention, the conductive means of the inventive connector which couples the leads of the fetal scalp electrode through the connector body also couples to the cable a reference voltage derived from the body of the patient. In one embodiment of the present invention, such a conductive means comprises a plurality of electrically isolated components from a single wiring frame. The connector body is molded about the plurality of wiring frame components to insulate each from the other. Advantageously the use of a single wiring frame in this capacity permits the manufacture of a connector in a very simple and economical fashion utilizing a minimum of different components. When analyzed in this light, the inventive connector comprises exclusively the components of a single wiring frame and an insert molded connector body formed thereupon.

In one embodiment, the wiring frame components comprise an electrically conductive signal pathway through the connector body corresponding to each lead of the fetal electrode. The signal pathway terminates in first and second ends that project from the connector body. The first end of the signal pathway is formed into a lead contact for electrically engaging a lead of the fetal scalp electrode. Preferably, the lead contact emerges from the conductor body at a point between the retention stub and the retention recess when these are engaged. The placement of a lead from the fetal electrode therebetween and the engagement of same both secures the lead to the connector and establishes the required electrical coupling for signals from the fetal scalp electrode.

The second end of each signal pathway is formed into a cable conductor contact site for electrically engaging a corresponding signal carrying conductor of the cable connected to the electronic monitor. Typically, where the fetal scalp electrode includes two leads, a pair of signal pathways according to the first conductive pathway described above are provided and embedded in the connector body.

The wiring frame components embedded in the connector body also comprise an electrically conductive reference pathway distinct in structure and function from the signal pathways already described. The reference conductive pathway passes through the connector body and terminates in first and second ends which are exposed on its exterior. The first end of the reference pathway is formed into a reference contact by which to effect an electrical reference coupling with the body of the patient. The second end of the second conductive pathway is formed into a reference conductor contact site for electrically engaging a reference conductor of the cable attached to the electrical monitor. In this manner a reference voltage derived from the reference contact is coupled through the inventive connector to the electronic monitor.

The reference contact itself comprises a plurality of structure for effecting the electrical reference coupling required In one of these, the reference contact comprises a reference plate disposed flush with the surface of the connector body on the side thereof that is place against the skin of the patient. Through this structure a medical practitioner may use the inventive connector either with or without a conductive gel to secure the needed reference voltage.

Alternatively, or in addition thereto, the reference contact of the inventive connector comprises a reference projection located within a receptacle formed in the connector body to receive male snap element that is electrically coupled to the body of the patient. Such a male snap element may take the form of the snap of an adhesive electrical contact patch, such as that already described.

In a preferred embodiment of the inventive connector, the connector body includes a number of features which contribute to the ease of its use. In one embodiment, the connector body comprises a generally flat lower surface which is designed to be placed against the body of the patient and an upper surface on the opposite side thereof. An upstanding rib is formed on the upper surface disposed generally parallel to the pivotable retention wing when the retention wing is in an engaged position against the connector body. The rib thus affords additional purchase on the connector body when the first and second retention structures are forced into resilient engagement with each other.

In addition a detachment tab may be formed at the end of each retention wing. By projecting generally in the plane of the wing beyond the first cooperating structure and beyond the end of the connector body when the retention wing is in its engaged position, the detachment tabs afford additional purchase on the retention wing to facilitate detachment of the first and second retention structures by pivoting the retention wing out of its engaged position. The retention wing is so designed as to be pivotable in a plane generally parallel to the lower surface of the connector body. Optionally a stabilization flange may be formed at selected portions of the periphery of that lower surface in order to give the connector body a broader base as it rests in position against the body of the patient.

As an additional contribution to the stability of the inventive conductor, a stabilization means may be provided for securing the connector to the body of the patient. In one embodiment such as stabilization means takes the form of a recess formed in the lower surface of the connector body and capable of receiving the snap portion of an adhesive skin electrode patch.

The inventive connector is thus a device advantageously capable of being manufactured in a very simple process at an extremely low cost. That method of manufacture is also contemplated as part of the present invention, but need not be elucidated further here. Simplicity and low cost render the inventive connector truly disposable.

Nevertheless, despite its diposability, the inventive connector is easily utilized. It does not employ spring biased lead clips, but relies entirely upon cooperating lead retention components which resiliently snap together to effect a secure mechanical and electrical interconnection of the leads of the fetal electrode with the connector.

In addition, the inventive connector affords a medical practitioner a full range of options as to whether, and if so, the manner in which to couple a reference voltage derived from the skin of the patient to an electronic monitor utilized to display signals from the fetal scalp electrode. The connector can be applied directly to the skin utilizing a conductive gel or attached to an adhesive patch with a snap electrode on the upper surface thereof.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are therefore not to be considered limiting of its scope, the invention will be described with additional specificity and detail through the use of the accompanying drawings in which.

DETAILED DESCRIPTION OF THE PREFERRED EMBODIMENTS

Figure 1:
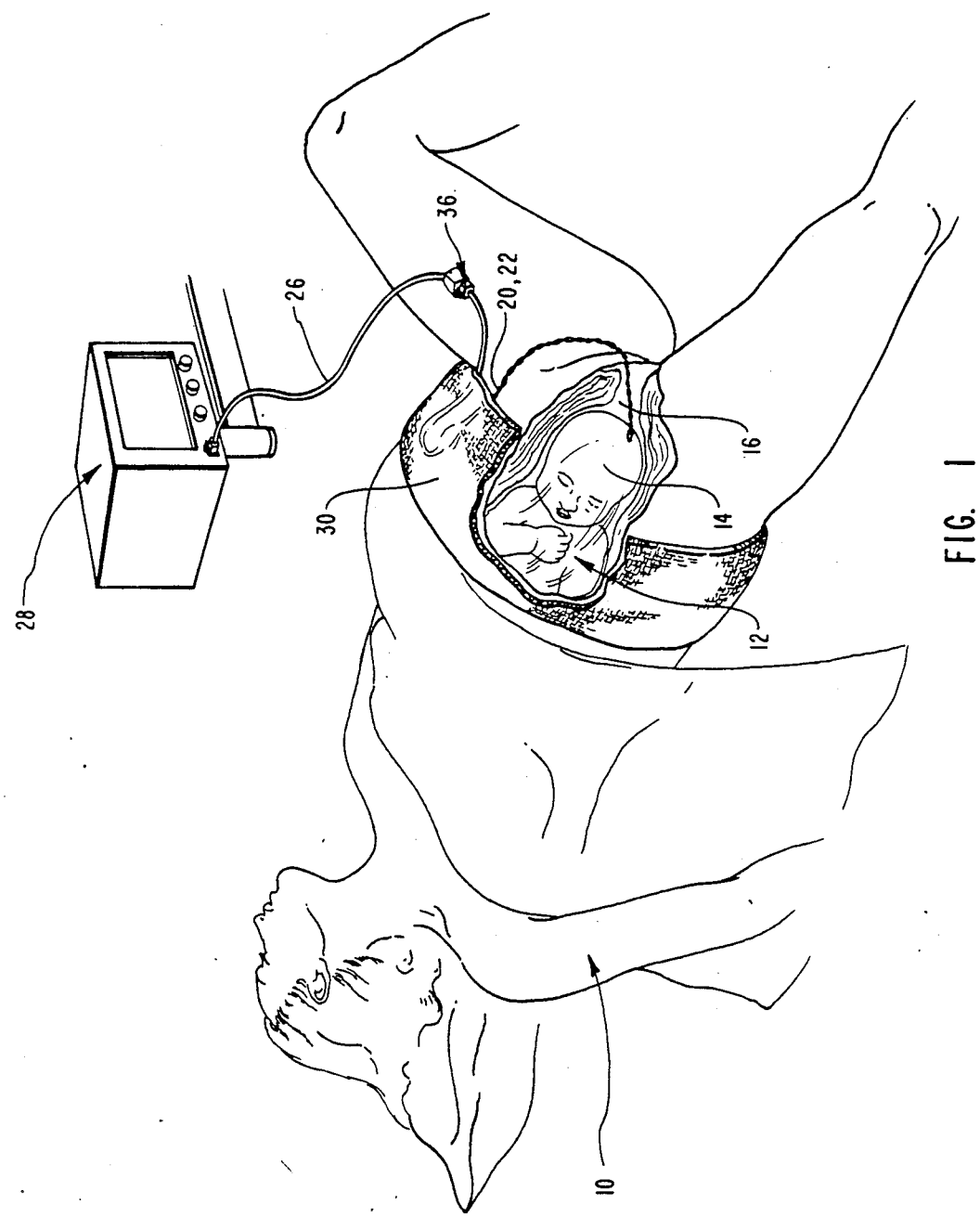
FIG. 1 is a schematic view of a first system for use during labor to monitor fetal condition using a fetal scalp electrode.

The inventive electrical connector will best be appreciated first by an understanding of the environment in which it finds utility. For this purpose, FIG. 1 schematically depicts a pregnant patient 10 during labor directed toward the delivery of a fetus 12. In FIG. 1, the head 14 of fetus 12 is oriented downwardly in the body of patient 10 so as to be accessible for examination by medical personnel through birth canal 16. Under such circumstances, where it is desired to do so, the heartbeat of the fetus can be monitored electronically.

Figure 2:
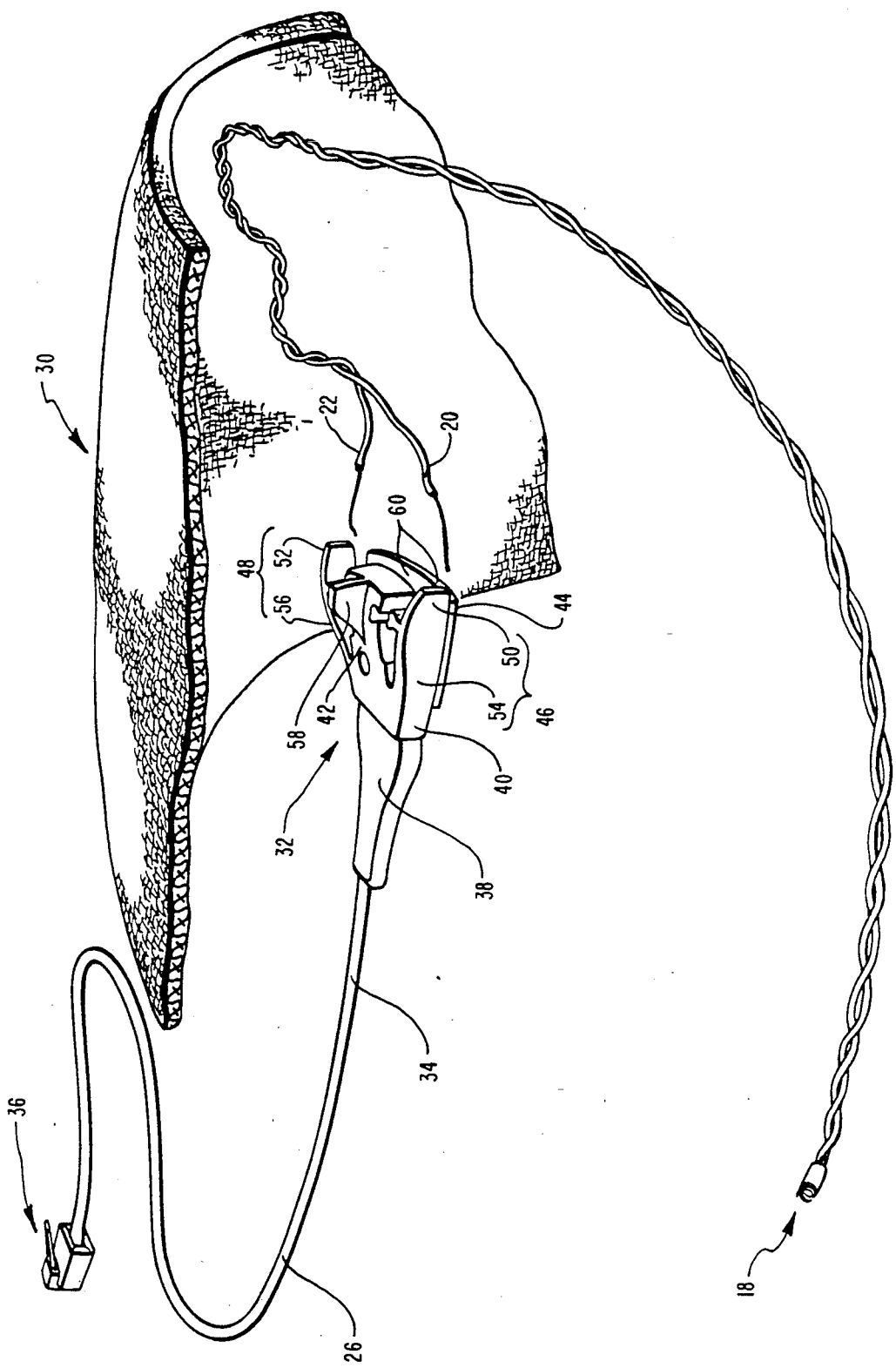
FIG. 2 is a disassembled perspective view of selected elements of the system illustrated in FIG. 1, including among those elements an embodiment of the inventive electrical connector.

Toward this end, an electrode viewed to best advantage in FIG. 2 as comprising a sharpened helical wire fetal scalp electrode 18 has been advanced through birth canal 16 and attached to the scalp of head 14 of fetus 12. Connected to fetal scalp electrode 18 are a pair of leads 20, 22, which pass through birth canal 16 carrying signals capable of reflecting the status of the fetal heart. These signals 22 are provided through a pair of cables 24, 26 interconnectable by a clip connector 36 to an electrical signal monitor 28 located in the labor room at a position remote from patient 10.

In the fetal monitoring system illustrated in FIG. 1, an elastic waistband 30 about patient 10 is used to secure at a fixed location the proximal ends of leads 20, 22 and the end of cable 26 remote from clip connector 36 and monitor 28. These ends of leads 20, 22 and of cable 26 are electrically coupled beneath waistband 30 by a first embodiment of an electrical connector 32 (not shown in FIG. 1) embodying teachings of the present invention.

As appreciated in additional detail in FIG. 2, the end 34 of cable 26 remote from clip connector 36 is permanently secured to electrical connector 32 within an insulative sleeve 38. The manner of this interconnection will be explored in detail subsequently. While during operation of the fetal monitoring system, leads 20, 22 are mechanically secured to electrical connector 32 and thereby electrically coupled therethrough to cable 26, leads 20,22 are for illustrative purposes in FIG. 2 shown free of electrical connector 32, as would be the case when the fetal monitoring system illustrated was in the process of being assembled.

A brief orientation to the exterior of electrical connector 32 will be in order prior to exploring an alternative configuration of a fetal monitoring system utilizing electrical connector 32.

Preferably, electrical connector 32 comprises a single, integrally formed injection molded connector body 40 which is distinct from sleeve 38. Connector body 40 is insert molded about a plurality of electrically conductive pathways which do not appear in FIG. 2, but will be illustrated and discussed subsequently. In an advantageous aspect of the present invention and its method of manufacture, these electrically conductive pathways can be fabricated from a single lead frame, thereby rendering the construction of electrical connector 32 extremely efficient and readily susceptible to mass assembly line practices.

Connector body 40 comprises an upper surface 42 and on the opposite side therefrom a generally planar lower surface 44 designed for placement against the body of patient 10. It is through lower surface 44 that a reference voltage for use by monitor 28 is derived and communicated through cable 26 thereto. In the configuration of the fetal monitoring system shown in FIG. 2, the development of such a reference voltage is by way of the placement of lower surface 44 in direct contact with the skin of patient 10 beneath waistband 30. As mentioned earlier, a conductive gel is useful in this process, but many practitioners now proceed without using such.

A pair of lead retention wings 46, 48 are disposed on opposite sides of connector body 48 integrally formed therewith. Retention wings 46, 48 are generally planar in construction, having free ends 50, 52, respectively, but being attached to connector body 40 at pivoted ends 54, 56, respectively. By this construction, retention wings 46, 48 are pivotable from connector body 40 in a plane generally parallel to lower surface 44 thereof. By way of reference, and through the pivoting thusly afforded to retention wings 46, 48, each of these structures is capable of swinging away from connector body 40 or being pivoted into an engaged position (shown in the first instance FIG. 4) against connector body 40.

Also apparent, in FIG. 2, is an upstanding rib 58 integrally formed with connector body 40 on upper surface 42 thereof. Rib 58 is disposed generally parallel to retention 21 wings 46, 48 when these are in the engaged position thereof (see FIG. 4). The function of rib 58 is generally to afford enhanced leverage upon electrical connector 32 when retention wings 46, 48 and pivoted into the engaged position thereof. It is in such a position that the proximal ends of leads 20, 22 of fetal scalp electrode 18 are secured to electrical connector 32 in a manner to be described in additional detail.

In order to add stability to electrical connector 32 when positioned with lower surface 44 against the body of a patient, connector body 40 is provided with an outwardly extending stabilization flange 60 at selected locations about the periphery of lower surface 44. Stabilization flange 60 also assists in the rapid and precise pivoting of retention wings 46, 48 into the engaged positions thereof by providing a support surface upon which retention wings 46, 48 can approach that engaged position.

Figure 3:
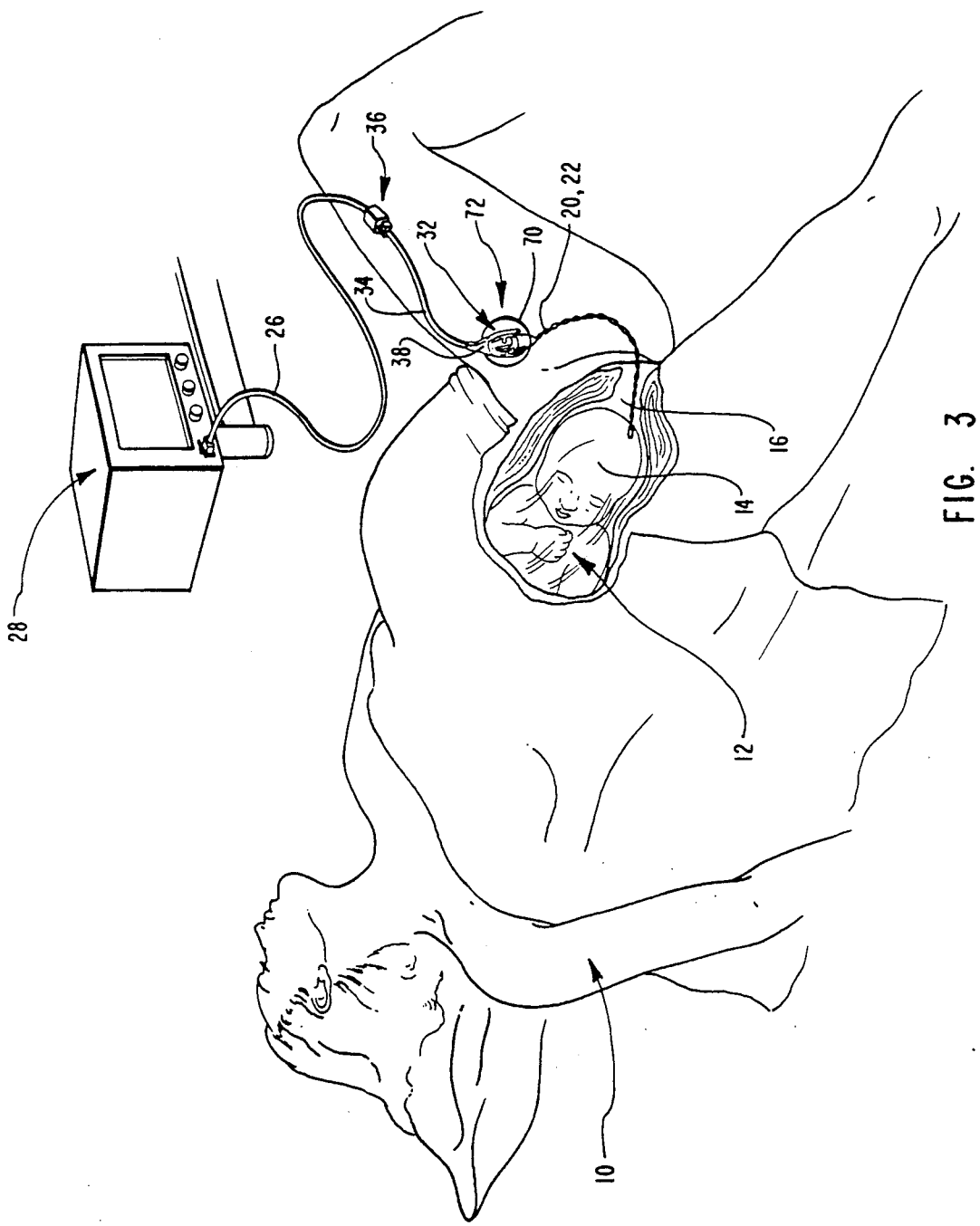
FIG. 3 is a perspective view of a second system like the system illustrated in FIG. 1, but employing an adhesive electrode patch.
Figure 4:
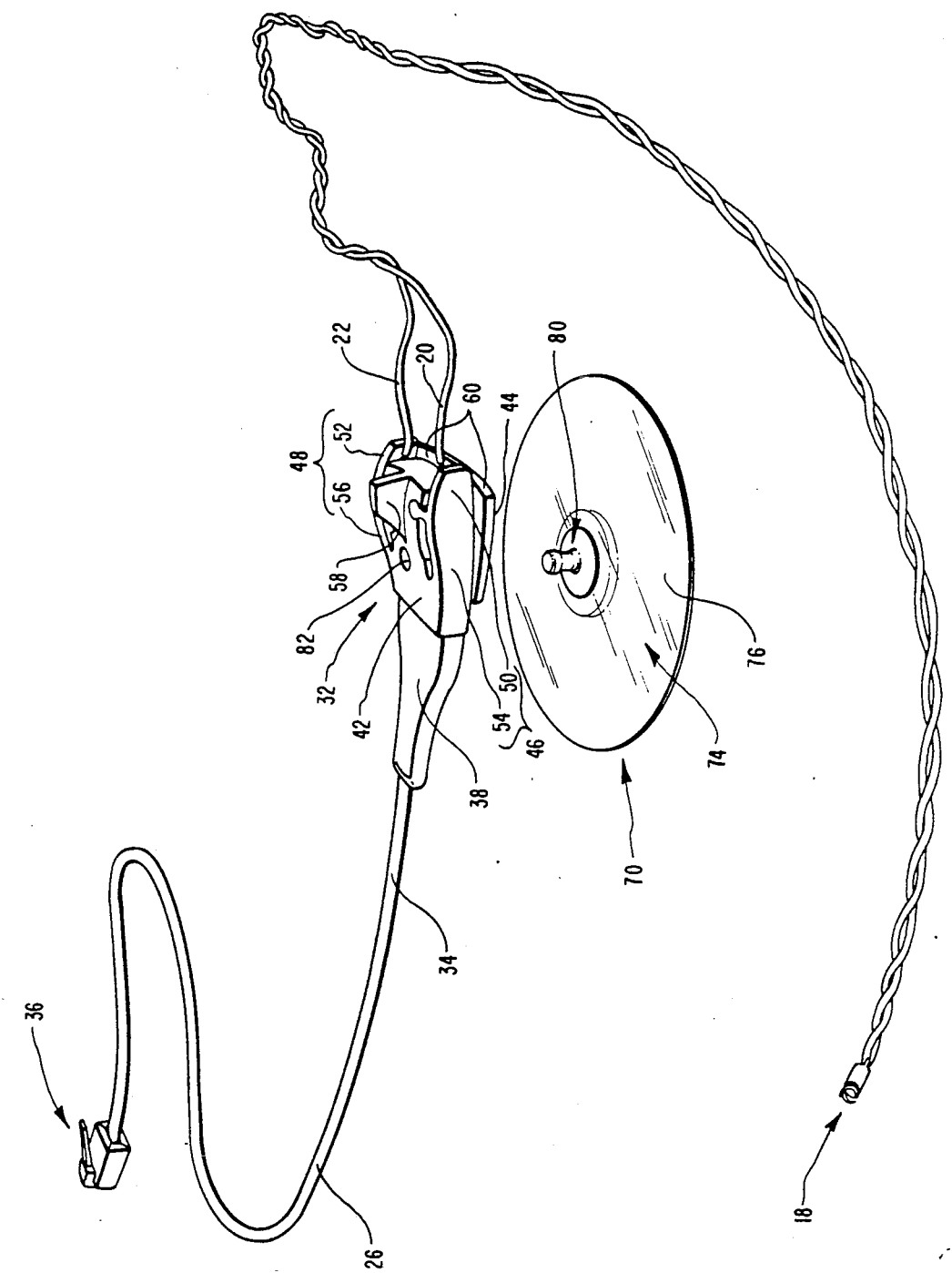
FIG. 4 is a perspective partially disassembled view of selected elements of the system illustrated in FIG. 3.

A second configuration of a fetal monitoring system incorporating an inventive electrical connector, such as electrical connector 32, is illustrated in relation to FIGS. 3 and 4. There, identical structures to those illustrated in FIGS. 1 and 2 are referred to by the corresponding reference characters already employed. Signals from fetal electrode 18 are communicated over leads 20, 22 to electrical connector 32 where the signals are coupled to cables 24, 26 for display on monitor 28.

In the case of the system illustrated in FIG. 3, however, electrical connector 32 with leads 20, 22 and cable 26 connected thereto is stably positioned through use of an adhesive electrode patch 70, which is shown as being adhered to the thigh 72 of patient 10. As best appreciated by reference to FIG. 4, electrode patch 70 includes a planar portion 74 having a top surface 76 and a bottom surface 78 (not visible in FIG. 4) to which a contact adhesive is applied. Centrally disposed on top surface 76 of planar portion 74 is a male snap fastener element 80, which is electrically coupled through planar portion 74 to the bottom surface thereof.

Thus, when electrode patch 70 is secured to the skin of a patient, male snap fastener element 80 becomes electrically coupled to the body of the patient, providing ready access through a corresponding snap receptacle, clip, or other attachment means to a reference voltage. Such a cooperating snap receptacle is formed through connector body 40 appearing at top surface 42 thereof as aperture 82. When received into the end of aperture 82 at lower surface 44 of electrical connector 32 (see FIGS. 6 and 7) male snap fastener element 80 is coupled by suitable electrically conducting pathways to a conductor in cable 26 designed to communicate a reference voltage to monitor 28.

Figure 5:
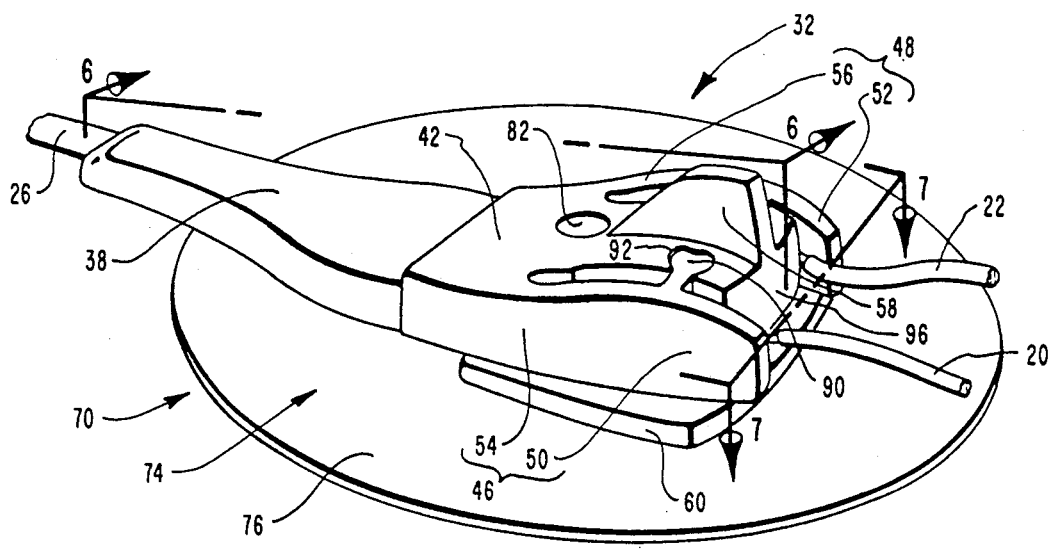
FIG. 5 is a perspective view of an electrical connector embodying teachings of the present invention and secured to an adhesive electrode patch.
Figure 6:
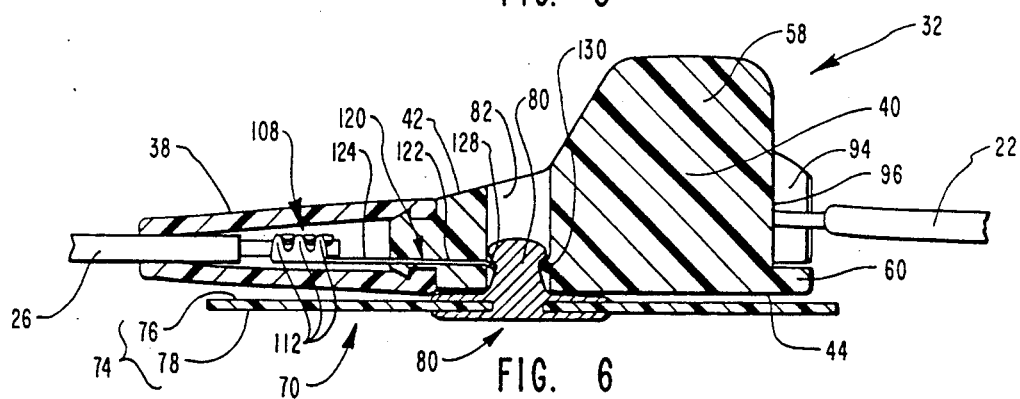
FIG. 6 is a cross-sectional plan view of the electrical connector and adhesive electrode patch of FIG. 5 taken along section line 6—6 appearing therein.
Figure 7:
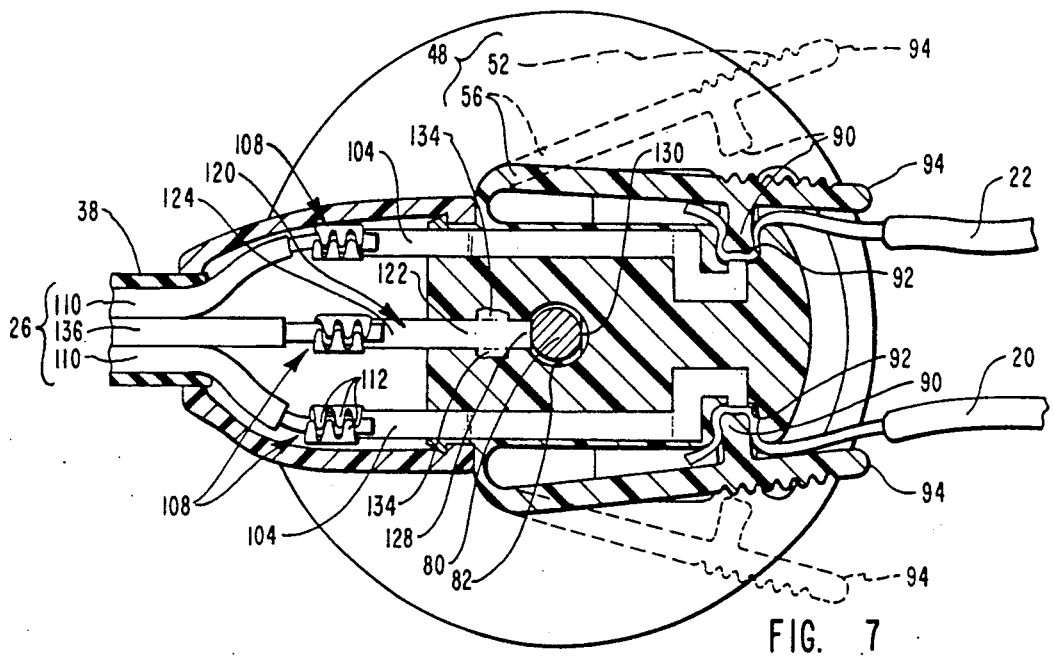
FIG. 7 is a cross-sectional plan view of the electrical connector and adhesive electrode patch of FIG. 5 taken along section line 7—7 appearing therein.
Figure 8:
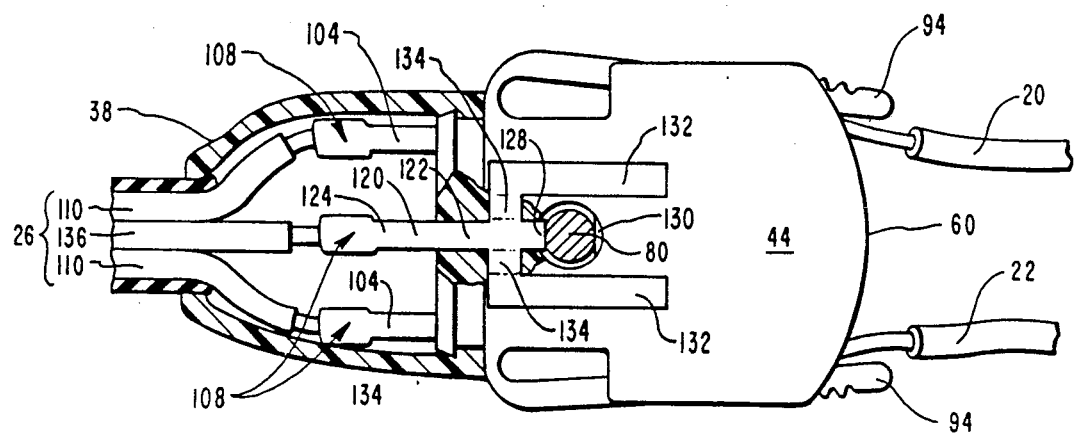
FIG. 8 is a partially broken away view of the surface of the electrical connector of FIG. 5 designed to be placed against the skin of a pregnant patient.
Figure 9:
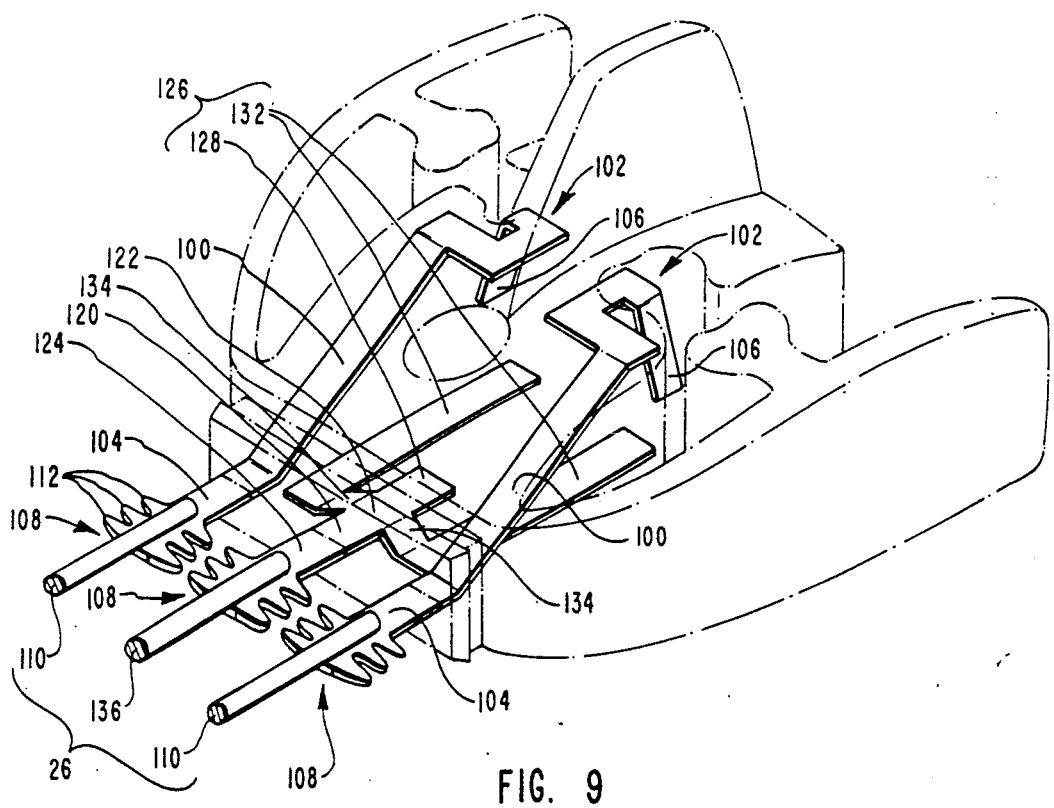
FIG. 9 is a perspective view of the electrical connector of FIG. 5 in which, for clarification purposes, selected interior elements thereof are depicted in solid lines and the exterior thereof is depicted in phantom lines.

A further in depth understanding of the structure and operation of electrical connector 32 can only be obtained by reference to the enlarged view of electrical connector 32 found in FIG. 5, the sectional views thereof shown in FIGS. 6 and 7, the bottom view shown in FIG. 8 and the perspective in partial phantom found in FIG. 9. In these figures, as previously, structures identical to those already discussed will be referred to by correspondingly identical reference characters.

According to one aspect of the present invention, an electrical connector, such as electrical connector 32, is provided with a lead retention means integrally formed with connector body 40 for securing leads 20, 22 of fetal scalp electrode 18 to connector body 40. Cooperating male and female lead retention structures are integrally formed on the exterior of connector body 40. The male and female lead retention structures are so configured as to grip one of leads 20, 22 located therebetween when the male and female lead retention structures engage each other.

As shown by way of example and not limitation, a lead retention stub 90 is integrally formed on the face of each of retention wings 46, 48 opposing connector body 40. Correspondingly a lead retention recess 92 is formed on the exterior of connector body 40 at a location to which retention stub 90 is directed when either of retention wings 46, 48 are pivoted into the engaged position thereof. Retention recess 92 is so configured as to be capable of receiving and gripping retention stub 90 in order to clamp one of leads 20, 22 in retention recess 92.

Thus, in order to secure each of leads 20, 22 to connector body 40, the lead is positioned beside connector body 40 traversing the opening to retention recess 92 and retention wing 46 or 48 as appropriate is pivoted toward connector body 40 so that retention stub 90 pushing lead 20 or 22 ahead of it enters and is held within retention recess 92. In the process of thusly effecting a mechanical attachment of leads 20, 22 to electrical connector 32, electrical coupling is simultaneously accomplished as will be described in full detail presently.

In the process just described of causing retention stub 90 to enter retention recess 92, rib 58 upstanding from upper surface 42 of connector body 40 is extremely useful. Rib 58 affords enhanced leverage upon the relatively small mass of connector body 40, thereby facilitating the urging of retention stub 90 with a lead 20 or 22 into retention recess 92.

Correspondingly, to assist in the disengagement of retention stub 90 from retention recess 92, a detachment tab 94 is provided at free end 50, 52 of each of retention wings 46, 48, respectively. Each detachment tab 94 extends beyond end 96 of connector body 40 when each of retention wings 46, 48 is in the engaged position thereof. Detachment tabs 94 thus offer enhanced leverage on each respective retention ring 46, 48 to facilitate disengagement of retention stub 90 from retention recess 92 by levering retention wing 46 away from connector body 40 so that it can pivot out of its engaged position. Doing so will then permit the removal of either lead 20 or 22 from the vacated retention recess 92. Due to the exterior design of the integrally formed components of connector body 40 the attachment and detachment of leads, such as lead 20, 22 is easily effected by medical personnel.

In another aspect of the present invention, conductive means are provided for electrically coupling leads 20, 22 of fetal scalp electrode 18 through connector body 40 to cable 26 when leads 20, 22 are secured to connector body 40 in the manner described above. A plurality of electrically isolated wiring frame components all derived from a single wiring frame are embedded in connector body 40 by having connector body 40 insert molded thereabout. These wiring frame components not only serve to effect electrical coupling between leads 20, 22 and appropriate conductors in cable 26, but also function to effect electrical reference coupling with the body of patient 10 by monitor 26.

As shown by way of example in FIGS. 8, the wiring frame components embedded in connector body 40 comprise a pair of electrically conductive signal pathways 100 which pass through connector body 40 and terminate in a first end 102 and a second end 104. These project from connector body 40 at generally opposite ends thereof. First end 102 of signal pathway 100 is formed into a flat lead contact 106 which is disposed in retention recess 92. Lead contact 106 is formed by being bent parallel to a wall of retention recess 92 from the point at which signal pathway 100 projects from connector body 40 thereinto. In this manner when one of leads 20, 22 is clamped in retention recess 92 it automatically makes electrical contact with lead contact 106.

Second end 104 of signal pathway 100 is formed into a cable conductor site 108 for electrically engaging a signal conductor 110 of cable 26. Any number of structures for such a cable conductor contact site known in the art can be utilized in this role, but as shown in FIGS. 6 and 7, cable conductor sites 108 comprise crimping fingers 112 to either side of second end 104 of signal pathway 100. Crimping fingers 112 are curled about signal conductor 110 to effect electrical coupling with cable 26.

Signal pathways 100 do not remain planar in their passage through connector body 40. Instead, signal pathways 100 enter connector body 40 and are ramped upwardly to first end 102. There first end 102 is bent downwardly as viewed in FIG. 9 to form lead contacts 106. Any number of patterns of signal pathways 100 could function in this regard, but that shown in FIGS. 8 has been found to be particularly suited to the shape of connector body 40 utilized in the embodiment of electrical connector 32 illustrated in this disclosure.

The wiring frame components embedded within connector body 40 further comprise an electrically conductive reference pathway 120 which passes through connector body 40 between a first end 122 and a second end 124, which are exposed on the exterior of connector body 40. First end 122 of reference pathway 120 comprises two functionally distinct branches, either or both of which effect an electrical reference coupling with the body of patient 10.

Thus, first end 122 of reference pathway 120 is formed into a reference contact 126 which includes a centrally disposed reference projection. This emerges from connector body 40 within aperture 82 for the purpose of effecting electrical coupling with male snap fastener 80. The retention of male snap fastener 80 in aperture 82 is enhanced by the integral formation of a ridge 130 on one side of aperture 182 opposing reference projection 128. This interaction of parts is best appreciated by reference to FIGS. 6-8 taken together.

Reference contact 126 formed in first end 122 of reference pathway 120 has, however, a second component which effects electrical referencing in a different manner. This component comprises a pair of reference plates 132 on either side of reference projection 128. Reference plates 132 are coupled to first end 122 of reference pathway 120 by transverse electrical interconnections 134. Transverse electrical connections 134 are bent downwardly from the point at which reference pathway 120 enters connector body 40, so as to permit reference plates 132 to be disposed flush with lower surface 44 of connector body 40. In this position, reference plates 132 can be placed against the skin of patient 10, as seen in FIG. 8, in order to permit the establishment of a reference voltage, even where a snap electrode, such as snap electrode 70, is not used. Such circumstances prevail in relation to the arrangement of a fetal monitoring system shown in FIGS. 1 and 2.

As with the specific layout of signal pathways 100, a number of alternate routings of reference pathway 120 are conceivable and are considered to be within the scope of the present invention.

The fabrication of signal pathways 100 and reference pathway 120 from a single planar lead frame, and the embedment using insert molding techniques of such wiring frame components in a single integrally formed connector body 40, represents an extremely simply and advantageously economic method of manufacturing a disposable electrical connector to be used with a fetal scalp electrode.

Second end 124 of reference pathway 120 is formed into a cable conductor contact site 108 similar in construction to those at second ends 104 of signal pathways 100. Nevertheless, the cable conductor contact site 108 at second end 124 of reference pathway 120 is specifically reserved for effecting electrical engagement with a reference conductor 136 of cable 26.

Electrical connector 32 as thus disclosed comprises a highly versatile tool which affords practioners the opportunity to use any known form of electrical referencing when coupling the leads from a fetal electrode to a monitor for displaying signals on those leads. The inventive electrical connector comprises two constituent parts: a molded body and electrically conductive lead frame components, all derived from a single lead frame. The disclosed device readily effects attachment to the leads of a fetal scalp electrode and equally readily permits the disengagement thereof.

For those unfamiliar with the manner in which a set of lead frame components, such as those illustrated in FIG. 8 are produced and incorporated into an injection molded body, brief reference will be made to the series of schematic developments shown in FIGS. 10-14. The lead frame components initially assume the form of a thin ribbon 140 of conductive material. Ribbon 140 exhibits the thickness of the final electrically conductive pathways, such as signal pathways 100 and reference pathway 120, to be embedded in the conductor body.

Figure 10:
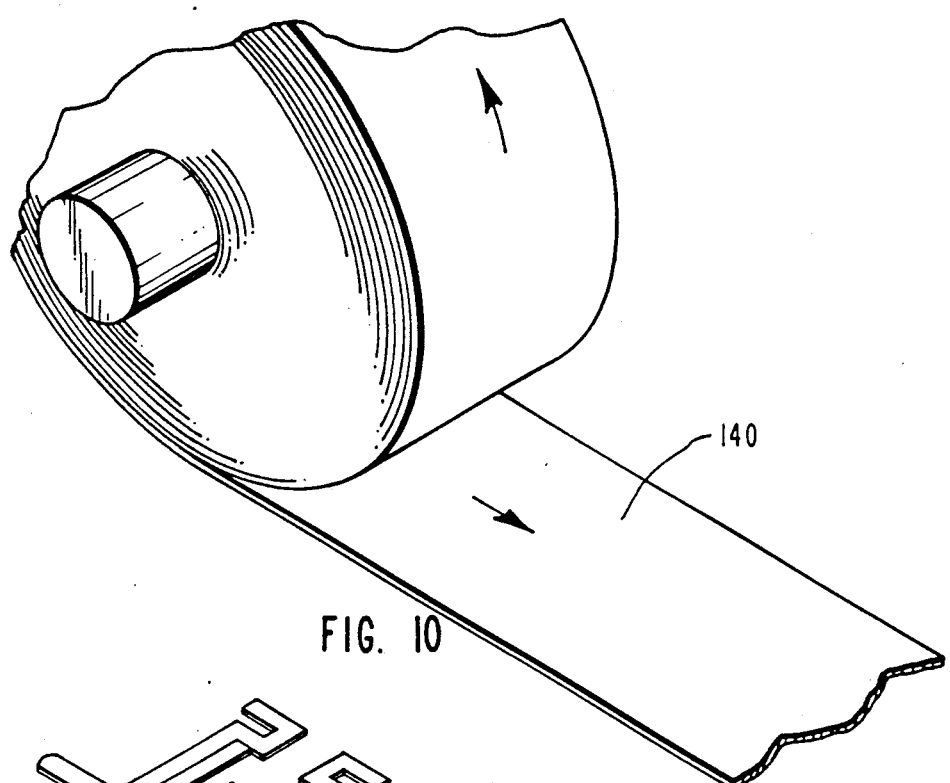
FIGS. 10–14 are schematic views illustrating the steps utilized to manufacture the electrical connector of FIG. 5 according to the teachings of the present invention.
Figure 11:
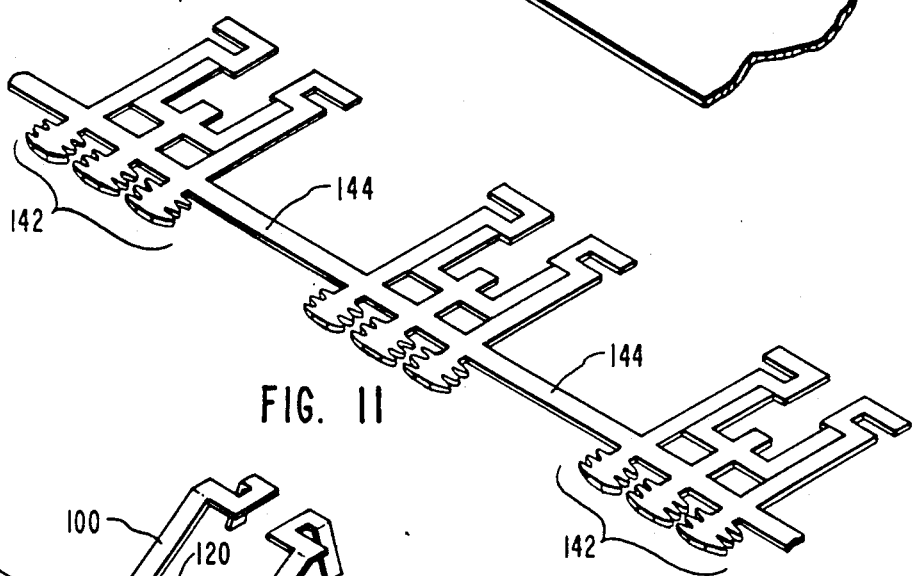
Figure 12:
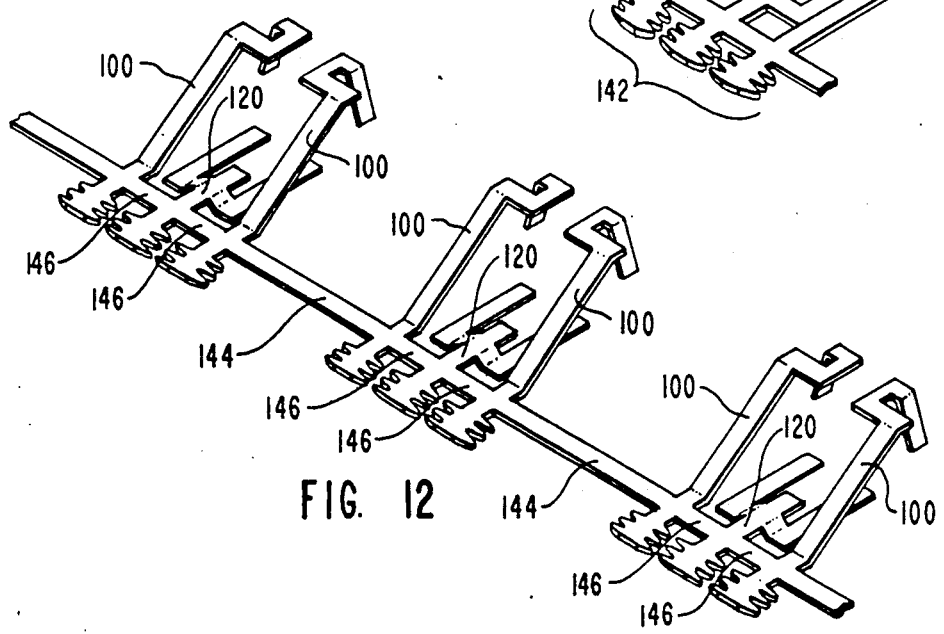
Figure 13:
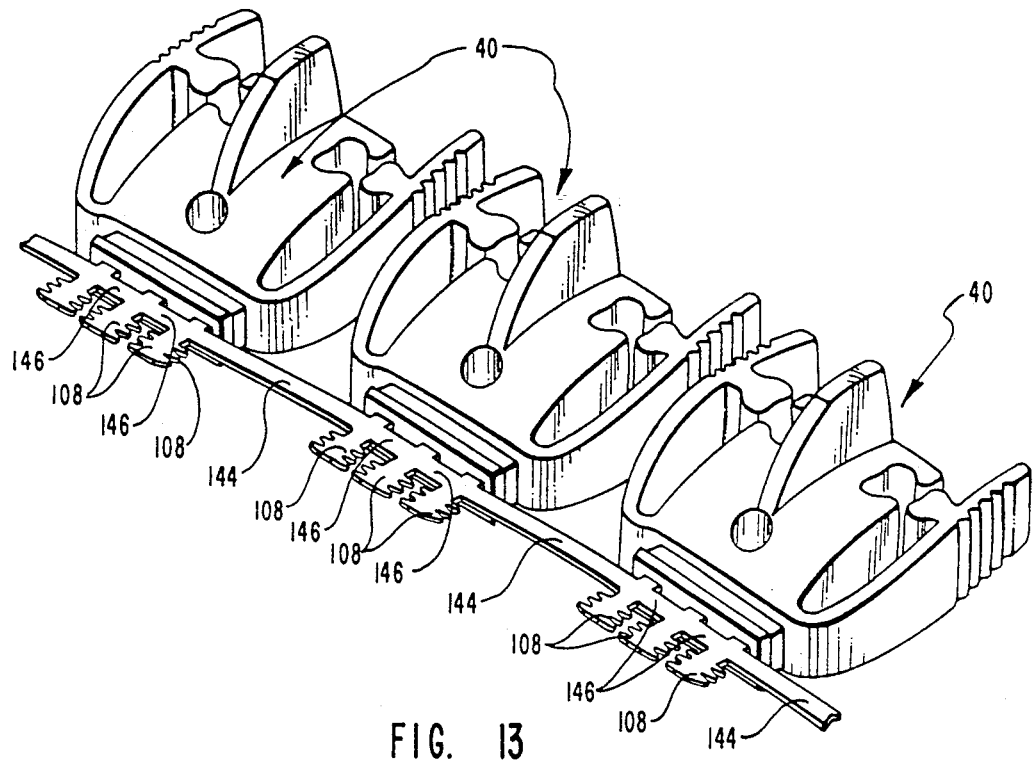
Figure 14:
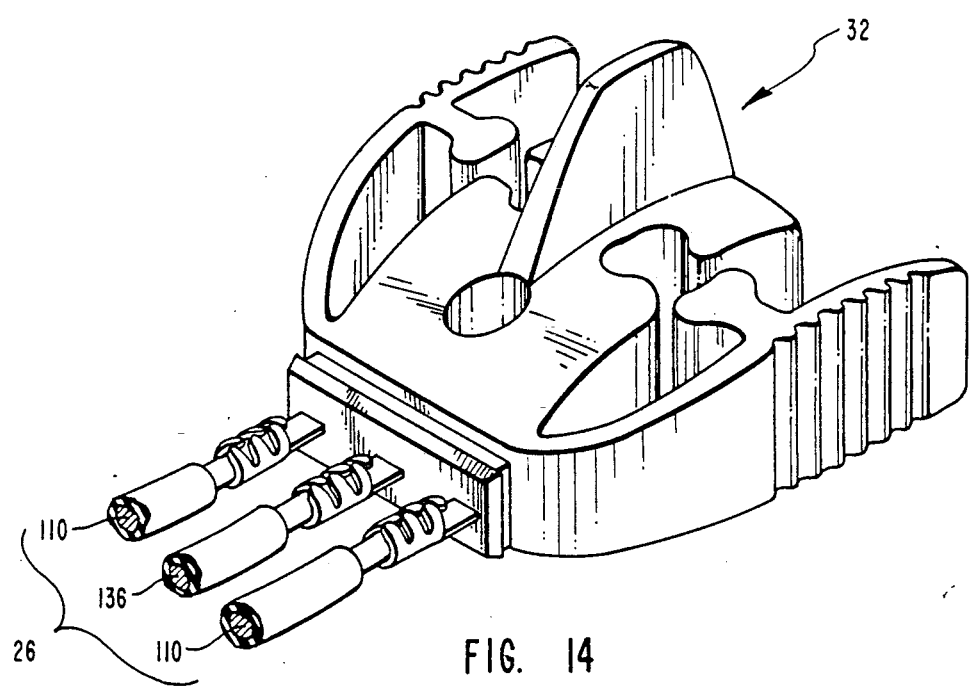

Thereafter, as shown in FIG. 10, successive identical lead frame patterns 142 are stamped out from ribbon 140 but left interconnected by carrier strips 144. Then, all desired bending of the lead frame components in each lead frame pattern 142 is undertaken. As shown in FIG. 11, conneced by carrier strips 144, a plurality of electrically conductive pathways inclusive of signal pathways 100 and reference pathway 120 result. Within each lead frame pattern 142, and between signal pathways 100 and reference pathway 120, is a structural support 146 which is aligned with carrier strip 144.

Thereafter, each lead frame pattern 142 is set in a mold (not shown) which is used to form carrier body 40. As shown in FIG. 11, successive carrier bodies 40 remain connected by carrier strip 144, and structural supports 146 interconnect cable conductor sites 108. Crimping fingers 112 have yet to be curled into engagement with any cable conductor. The separation of carrier bodies by the removal of carrier strips 144 therebetween follows. The severing of structural supports 146 and the attachment of signal conductors 110 and reference conductor 136 of cable 26 substantially completes the manufacture of electrical conductor 32.

Accordingly, the present invention also contemplates a method for manufacturing an electrical connector for use with a patient during labor to couple signals from the leads of a fetal scalp electrode to a cable connected to an electrical signal monitor. The method comprises the steps of forming a wiring frame from a planar sheet of conductive material. The wiring frame comprises an electrically conductive signal pathway corresponding to each of the leads of the fetal scalp electrode, an electrically conductive reference pathway, and a structural support between both. Thereafter the method contemplated comprises bending of the signal pathways out of the plane of the wiring frame to form lead contacts for electrically engaging the leads of the fetal scalp electrode pathway corresponding to each of the leads of the fetal scalp electrode, an electrically conductive reference pathway, and a structural support between both. Thereafter the method contemplated comprises bending of the signal pathways out of the plane of the wiring frame to form lead contacts for electrically engaging the leads of the fetal scalp electrode and to form a reference contact for establishing electrical reference coupling to the body of the patient. This is followed by insert molding about the signal pathways a connector body comprised of an electrically insulative material. The structural supports are removed from between the signal pathways and an end of each signal and reference pathway is connected to a conductor of the cable.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Patent is:

1. An electrical connector for use during labor to couple signals from leads of insulated conductors of a fetal scalp electrode to a cable connected to an electrical signal monitor, said connector comprising:
   a. a connector body;
   b. lead retention means molded as an integral part of said connector body for releasably securing with a snap fit the leads of said insulated conductor of the fetal scalp electrode to said connector body; and
   c. conductive means embedded within said connector body for electrically coupling the leads of the fetal scalp electrode through said connector body to the cable when the leads are secured by said lead retention means to said connector body said conductive means comprising:
  (i). a lead contact located at said lead retention means for electrically engaging a lead of the fetal scalp electrode secured thereby to said connector body;
  (ii). a signal conductor contact site located exterior of said connector body for electrically engaging a signal carrying conductor of the cable;
  (iii). an insulated electrically conductive pathway extending from said lead contact through said connector body to said signal conductor contact site; and
  (iv). means for effecting electrical reference coupling of a reference conductor of the cable with the body of the patient.

2. A connector as recited in claim 1, wherein said lead retention means comprises cooperating male and a female lead retention structures integrally formed on said connector body, said male and female retention structures being so configured as to grip a lead of the fetal scalp electrode placed therebetween when said male and female lead retention structures engage each other.

3. A connector as recited in claim 1, wherein said lead retention means comprises:
  a. a lead retention stub integrally formed at a first location on said connector body; and
  b. a lead retention recess formed on said connector body at a second location thereon, said retention recess being so located and configured as to be capable of receiving and gripping said retention stub to clamp a lead of the fetal scalp electrode in said retention recess.

4. A connector as recited in claim 3, wherein said retention stub is located on a lead retention wing integrally formed with and pivotal from said connector body into an engaged position wherein said retention stub is received in said retention recess.

5. A connector as recited in claim 4, wherein said conductive means comprises a lead contact projecting from said connector body into said retention recess for electrically engaging a lead of the fetal scalp electrode.

6. A connector as recited in claim 4, further comprising a detachment tab at a free end of said retention wing, said detachment tab projecting beyond said connector body when said retention wing is in said engaged position, thereby to afford secure leverage on said retention wing to facilitate detachment of said retention stub and retention recess when said retention wing is pivoted out of said engaged position.

7. A connector as recited in claim 1, further comprising stabilization means for securing said connector body to the body of the patient.

8. A connector as recited in claim 7, wherein said stabilization means comprises a snap receptacle for receiving a male snap fastener element attached to the body of the patient.

9. A connector as recited in claim 4, wherein said connector body comprises an upper surface and a generally planar lower surface for placement against the body of the patient.

10. A connector as recited in claim 9, further comprising an upstanding rib integrally formed with said connector body on said upper surface thereof, said rib being disposed generally parallel to said retention wing in said engaged position, whereby to afford secure leverage on said connector body when said retention wing is pivoted into said engaged position.

11. A connector as recited in claim 9, wherein said retention wing is pivotal in a plane generally parallel to said lower surface of said connector body.

12. A connector as recited in claim 9, further comprising a stabilization flange outwardly extending from said connector body at selected locations on the periphery of said lower surface thereof.

13. An electrical connector for use during labor and delivery to couple signals from leads of a fetal scalp electrode to a cable connected to an electrical signal monitor, said connector comprising:
  a. a plurality of electrically isolated wiring frame components from a single wiring frame; and
  b. a connector body insert molded about said plurality of wiring frame components and wherein said connector body comprises an upper surface and on an opposite side therefrom a generally planar lower surface for placement against the body of the patient, and wherein said connector body further comprises:
    (i) a pair of wings integrally formed with said connector body and pivotal therefrom in a plane generally parallel to said lower surface into an engaged position against said connector body; and
    (ii) an upstanding rib integrally formed with said connector body on said upper surface thereof, said rib being disposed generally parallel to said wing in said engaged position thereof.

14. A connector as recited in claim 13, further comprising lead retention means integrally formed with said connector body for securing a lead of the fetal scalp electrode to said connector body at said lead contact.

15. A connector as recited in claim 13, wherein said wiring frame components further comprising an electrically conductive reference pathway through said connector body, said reference pathway terminating in first and second ends exposed on the exterior of said connector body, said first end of said reference pathway being formed into a reference contact for effecting an electrical reference coupling with the body of the patient, and said second end of said reference pathway being formed into a cable conductor contact site for electrically engaging a conductor of the cable.

16. A connector as recited in claim 15, wherein said reference contact comprises a reference plate disposed flush with a surface of said connector body on a side thereof to be placed against the skin of the patient.

17. A connector as recited in claim 15, wherein said reference contact comprises a reference projection located within a snap receptacle formed in said connector body for receiving a male snap fastener electrically coupled to the body of the patient.

18. A connector as recited in claim 16, wherein said reference contact further comprises a reference projection located within a snap receptacle formed in said connector body for receiving a male snap fastener element coupled to the body of the patient, and wherein said reference pathway further comprises an electrical interconnection between said reference plate and said reference projection.

19. An electrical connector for use during labor to couple signals from leads of a fetal scalp electrode to an electrical signal monitor, said connector comprising:
  a. a connector body;
  b. a cable attached to said connector body for coupling to the monitor;

c. lead retention means formed as an integral part of said connector body for securing the leads of the fetal scalp electrode to said connector body, said lead retention means comprising:
   (i) a lead retention stub located on a lead retention wing integrally formed with and pivotal from said connector body; and
   (ii) a lead retention recess formed in said connector body, said retention recess being so located and configured so as to receive and grip said retention stub to clamp a lead of the fetal scalp electrode in said retention recess; and
d. conductive means for electrically coupling the leads of the fetal scalp electrode through said connector body to the cable when the leads are secured by said lead retention means to said connector body.

20. A connector as recited in claim 19, wherein said conductive means comprises a lead contact projecting from said connector body into said retention recess for electrically engaging a lead of the fetal scalp electrode.

21. A connector as recited in claim 19, wherein:
a. said cable comprises a signal conductor for communicating a signal from a lead of the fetal scalp electrode to the monitor; and
b. said conductive means comprises an electrically conductive signal pathway through said connector body, said signal pathway terminating in first and second ends projecting from said connector body, said first end of said signal pathway being formed into a lead contact for electrically engaging the lead of the fetal scalp electrode, and said second end of said signal pathway being formed into a signal conductor contact site for electrically engaging said signal conductor of said cable.

22. A connector as recited in claim 21, wherein:
a. said cable further comprises a reference conductor for communicating to the monitor an electrical reference voltage derived from the body of the patient; and
b. said conductive means further comprises an electrically conductive reference pathway through said connector body, said reference pathway terminating in first and second ends exposed on the exterior of said conductive body, said first end of said reference pathway being formed into a reference contact for effecting an electrical reference coupling with the body of the patient, and said second end of said reference pathway being formed into a reference conductor contact site for electrically engaging said reference conductor of said cable.

23. A connector as recited in claim 22 further comprising a snap receptacle for receiving a male snap fastener element secured to the body of the patient, and wherein said reference contact is located within said snap receptacle.

24. A connector as recited in claim 22, further comprising an electrically insulating sleeve disposed about the cable and the connector body at said cable conductor contact sites.

25. An electrical connector for use during labor to couple signals from a lead of a fetal scalp electrode to an electrical signal monitor, said connector comprising:
a. a connector body;
b. a cable attached to said connector body for coupling to the monitor, said cable comprising:
   (i) a signal conductor for communicating a signal from a lead of the fetal scalp electrode to the monitor; and
   (ii) a reference conductor for communicating to the monitor an electrical reference voltage derived from the body of the patient;
c. lead retention means molded as an integral part of said connector body for releasably securing the leads of the fetal scalp electrode to said connector body with a snap fit; and
d. a plurality of electrically isolated wiring frame components from a single wiring frame, said connector body being insert molded about said plurality of wiring frame components and said wiring frame components comprising an electrically conductive signal pathway through said connector body, said signal pathway terminating in first and second ends projecting from said connector body, said first end of said signal pathway being formed into a lead contact for electrically engaging a lead of the fetal scalp electrode, and said second end of said signal pathway being formed into a signal conductor of said cable, and wherein said wiring frame components further comprise an electrically conductive reference pathway through said connector body, said reference pathway terminating in first and second ends exposed on the exterior of said connector body, said first end of said reference pathway being formed into a reference contact for effecting an electrical reference coupling with the body of the patient, and said second end of said reference pathway being formed into a reference conductor site for electrically engaging said reference conductor of said cable.

26. A connector as recited in claim 25, wherein said reference contact comprises a reference projection located within a snap receptacle formed in said connector body for receiving a male snap fastener element electrically coupled to the body of the patient.

27. A connector as recited in claim 25, wherein said reference contact comprises a reference plate disposed flush with the surface of said connector body on the side thereof to be placed disposed against the skin of the patient.

28. A connector as recited in claim 27, wherein said reference contact further comprises a reference projection located within a snap receptacle formed in said connector body for snappingly receiving a male snap fastener element electrically coupled to the body of the patient, and wherein said reference pathway further comprises an electrical interconnection between said reference plate and said reference projection.

29. A connector as recited in claim 25, wherein said lead retention means comprises:
a. a lead retention stub integrally formed at a first location on said connector body; and
b. a lead retention recess formed on of said connector body at a second location thereon, said retention recess being so located and configured as to be capable of receiving and gripping said retention stub to clamp a lead of the fetal scalp electrode in said retention recess.

30. A connector as recited in claim 29, wherein said retention stub is located on a lead retention wing integrally formed with and pivotal from said connector body into an engaged position wherein said retention stub is received in said retention recess.

31. An electrical connector for use with a patient during labor to couple signals from the leads of a fetal scalp electrode to an electrical signal monitor, said connector comprising:
   a. a connector body having an upper surface and on the opposite side therefrom a generally planar lower surface for placement against the body of the patient;
   b. a lead retention wing integrally formed with said connector body and pivotal therefrom in a plane generally parallel to said lower surface thereof into an engaged position against said connector body;
   c. an upstanding rib integrally formed with said connector body on said upper surface thereof, said rib being disposed generally parallel to said wing in said engaged position thereof;
   d. a cable attached to said connector body for coupling to the monitor, said cable comprising:
      (i) a signal conductor for communicating a signal from a lead of the fetal scalp electrode to the monitor; and
      (ii) a reference conductor for communicating to the monitor an electrical reference voltage derived from the body of the patient;
   e. a plurality of electrically isolated wiring frame components from a single wiring frame, said connector body being insert molded about said plurality of wiring frame components, and said wiring frame components comprising:
      (i) an electrically conductive signal pathway through said connector body, said signal pathway terminating in first and second ends projecting from said connector body, said first end of said signal pathway being formed into a lead contact for electrically engaging a lead of the fetal scalp electrode, and said second end of said signal pathway being formed into a signal conductor contact site for electrically engaging said signal conductor of said cable; and
      (ii) an electrically isolated conductive reference pathway through said connector body, said reference pathway terminating in first and second ends exposed on the exterior of said connector body, said first end of said reference pathway being formed into a reference contact for effecting an electrical reference coupling with the body of the patient, and said second end of said reference pathway being formed into a reference conductor contact site for electrically engaging said reference conductor of said cable;
   f. a lead retention stub integrally formed on said retention wing; and
   g. a lead retention recess formed in the exterior of said connector body at a second location thereon, said lead retention recess being so located and configured as to be capable of receiving and gripping said retention stub to clamp a lead of the fetal scalp electrode in said retention recess when said retention wing is in said engaged position thereof.

32. A connector as recited in claim 31, wherein said retention stub is located on a lead retention wing integrally formed with and pivotal from said connector body into an engaged position wherein said retention stub is received in said retention recess.

33. A connector as recited in claim 31, wherein said reference contact comprises:
   a. a reference plate disposed flush with the surface of said connector body on the side thereof to be placed against the skin of the patient; and
   b. a reference projection located within a snap receptacle formed in said connector body for receiving a male snap fastener element electrically coupled to the body of the patient, and wherein said second conductive pathway further comprises an electrical interconnection between said reference plate and said reference projection.

* * * * *

UNITED STATES PATENT AND TRADEMARK OFFICE
CERTIFICATE OF CORRECTION

PATENT NO. : 5,046,965

DATED : September 10, 1991

INVENTOR(S) : JON N. NEESE et al.

It is certified that error appears in the above-identified patent and that said Letters Patent is hereby corrected as shown below:

```
Column 2, line 48, "undesireable" should be --undesirable--
Column 3, line 35, after "contact" delete ","
Column 5, line 17, after "required" insert --.--
Column 5, line 19, "is place" should be --is placed--
Column 5, line 27, after "receive" insert --a--
Column 5, line 65, after "and" insert --is--

Column 5, line 42, "purchase" should be --leverage--

Column 6, line 19, after "or" insert --can be--
Column 6, line 14, after "whether" insert --to use a reference
voltage contact--
Column 7, line 40, before "thereby" insert --are--
Column 7, line 63, after "surface 44" insert --is--
Column 8, line 10, "being" should be --are--
Column 11, line 66, "conneced" should be --connected--
Column 13, line 1, after "body" insert --,--
```

Signed and Sealed this

Tenth Day of August, 1993

Attest:

MICHAEL K. KIRK

Attesting Officer

Acting Commissioner of Patents and Trademarks